United States Patent [19]
Kosonen

[11] 3,937,217
[45] Feb. 10, 1976

[54] INTRAUTERINE CONTRACEPTIVE DEVICE

[75] Inventor: Ahti A. Kosonen, Pori, Finland

[73] Assignee: Outokumpu Oy, Helsinki, Finland

[22] Filed: Mar. 8, 1974

[21] Appl. No.: 449,245

[30] Foreign Application Priority Data
Mar. 19, 1973 Finland .............................. 847/73

[52] U.S. Cl. .............................................. 128/130
[51] Int. Cl.² .......................................... A61F 5/46
[58] Field of Search ............ 128/127, 128, 129, 130

[56] References Cited
UNITED STATES PATENTS

| | | | |
|---|---|---|---|
| 533,120 | 1/1895 | Ferguson | 128/130 |
| 3,454,004 | 7/1969 | Leininger et al. | 128/130 |
| 3,516,403 | 6/1970 | Cournut | 128/130 |
| 3,533,406 | 10/1970 | Tatum | 128/130 |
| 3,678,927 | 7/1972 | Soichet | 128/130 |

FOREIGN PATENTS OR APPLICATIONS 798,655 11/1968 Canada ............................. 128/130

Primary Examiner—Lawrence W. Trapp
Attorney, Agent, or Firm—Brooks Haidt Haffner & Delahunty

[57] ABSTRACT

An intrauterine contraceptive device, resembling the shape of T, deviating from that, however, by having in the end of a vertical arm a loop which is easy to compress for insertion and having in the upper end of the vertical arm two arms departing to opposite sides and jointed smoothly to the vertical arm so that the bending radius is relatively big, the angle between the horizontal and vertical arm being preferably smaller than 90°.

5 Claims, 5 Drawing Figures

U.S. Patent   Feb. 10, 1976   3,937,217
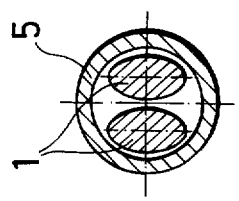
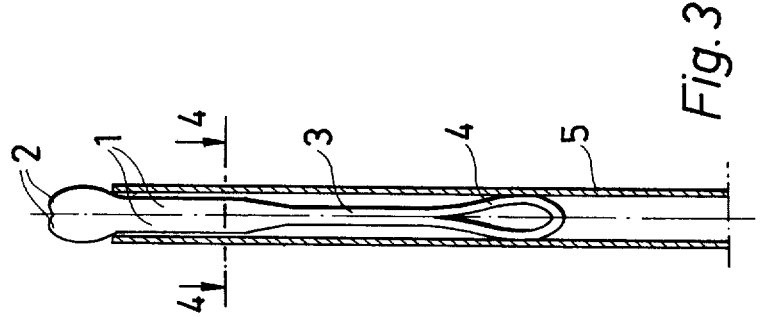
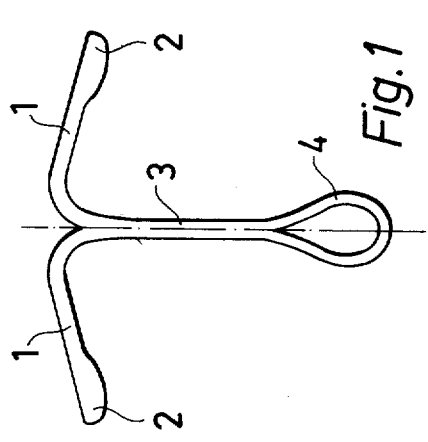
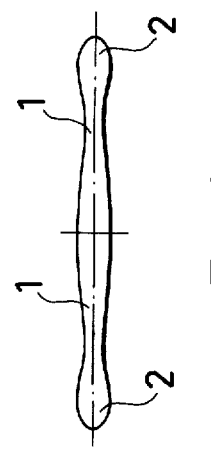
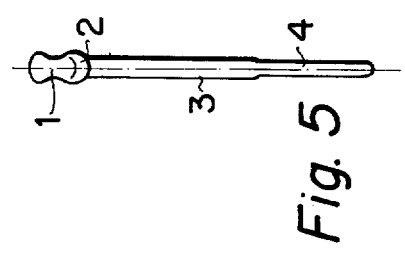

INTRAUTERINE CONTRACEPTIVE DEVICE

BACKGROUND OF THE INVENTION

This invention relates to an improved intrauterine contraceptive device. The object of the invention is to obtain a device which has a lower expulsion rate and is less irritative than other IUDs. There is a known IUD having the shape of a T according to U.S. Pat. No. 3,533,406. Its horizontal arms are placed into the upper part of the endometrial cavity near the fundus and the distance of the ends of horizontal arms is 30–35 mm corresponding to the size of the portion of the uterus. The vertical arm is relatively thin having a length of 28–36 mm. The purpose is that the device is completely placed into the endometrial cavity and the end of the vertical arm extends toward the cervical os when the crossbar of the T lies at the fundus of the uterus.

Statistics have revealed that the rate of bleeding and pain by the T device as well as by Lippes Loop is relatively high approximately 10 per cent calculated on the basis of 100 used women months. This is caused mainly by the rigidity of the mentioned devices. During the contraction of the uterus the high pressure is directed against the horizontal arms and when these arms in the T device only slightly deviate from the horizontal line a rather high pressure is needed to change its shape. This causes the relatively pointed ends of the horizontal arms to penetrate to the mucous membrane and uterus wall. This is also admitted in the above-mentioned patent which says: "X-rays studies indicate that the ends of crossbar will become slightly imbedded in the endometrium".

It is also evident that both the T and Lippes Loop are even in the vertical direction relatively rigid and cases have been found when the vertical arm of the T has penetrated into the uterus wall causing bleeding and pain.

The results of clinical tests of the T and especially by Lippes Loop show a relatively high rate of involuntary expulsions for patients wearing the device.

The object of this invention has been to decrease or eliminate the event rates mentioned above and get a higher continuation rate than other IUDs.

SUMMARY OF THE INVENTION

According to the invention there is now provided an intrauterine contraceptive device, somewhat like the shape of the letter T, deviating from that, however, by having in the end of a vertical arm a loop which is easy to compress for insertion and having in the upper end of the vertical arm two oppositely directed departing arms jointed smoothly to the vertical arm so that the bending radius is relatively big, the angle between the horizontal and vertical arm being preferably smaller than 90°.

DESCRIPTION OF THE DRAWINGS

FIG. 1 represents the side view of IUD and in

FIG. 2 the device is seen from above.

FIG. 3 represents the method of loading into the inserter tube and

FIG. 4 the cross-section in line 4—4 in FIG. 3.

FIG. 5 is a profile view of the IUD taken at a right angle to the view of FIG. 1.

DESCRIPTION OF THE PREFERRED EMBODIMENTS

It is the object of the present invention to decrease or eliminate the events of bleeding, pain, and involuntary expulsion mentioned above by:

a. giving a sufficient deviation to horizontal arms from the horizontal line so that the forces which uterus walls create during the contraction onto the tips 2 of these arms are able to bend the horizontal arms preventing them from penetrating easily into the uterus wall, b. joining the horizontal arms to the vertical arms smoothly and arranging a sufficient radius of curvature. In this way the possibility of any occurrence of plastic deformation is prevented during loading the device into an inserter tube as often occurs with the T device. This kind of curvature improves also the bending of horizontal arms when submitted to the lateral pressure of uterus wall during contraction, c. enlarging the tips 1 and of the horizontal arms and the portions of such arms adjacent the tips 2 to form a half-ball or a loop. It is performed to decrease further the lateral pressure to the tips of horizontal arms during the contraction of the uterus, d. forming the end 4 of the vertical arms remote from the horizontal arms into a loop. This is intended to eliminate the penetration of the end of the vertical arm 3 into the uterus wall. The loop increases the surface area of the end and consequently the surface pressure is decreased. Further, the vertical arm is partially made thinner preferably just above the end loop. This and the loop itself, which is also thinner than the vertical arm generally, increase the elasticity and enable an easy bending during the movement of the uterus.

In the present invention the purpose of the loop 4 in the end of the vertical arm 3 is also to minimize expulsions. The largest diameter of the loop is bigger than the inner diameter of the inserter tube 5. By loading the device into the inserter tube the loop 4 is pressed together and when inserted into the endometrium cavity the loop takes its original shape. The rounded lower part of the loop will be supported to the upper edges of the cervical os preventing by that way the device to slip down into the cervical os. Further, as the horizontal arms 1 are made elastic and curved downwards, the device will during the contraction of the uterus rather rise upwards than be pressed down. The device according to this invention has for example the further advantage compared with the mentioned T device that it can be loaded into the inserter tube 5 setting the horizontal arms 1 upwards. Using this loading method it is possible to decrease the diameter of the inserter tube 5 to a much smaller size than which is possible for the inserter tube of the T. This enables that the device according to this invention can be inserted to nulliparous women. Further, the well-rounded tips or loops 2 in the ends of horizontal arms 1 will cover the edges of the inserter tube 5 so that these sharp edges do not cause any damage during the insertion.

When the device according to this invention, especially through the loops or balls 2, dimensionally is larger than the T device it has a better mechanical contraceptive effect than the latter.

It will be understood that the present invention may be combined with other methods of contraception such as copper or copper alloys as presented in U.S. Pat. No. 3,563,235 to provide an improved effectiviness. The metal can be added in form of wire or sleeves.

What is claimed is:

1. An intrauterine contraceptive device for placement within the uterine cavity having a normally generally T-shaped configuration with a stem having two outwardly extending arms joined to the stem along a smoothly bent curved portion, said curved portion being flexible, said arms normally extending at acute angles with respect to said stem, said smoothly bent curved portion being bent on a sufficient radius of curvature for prevention of plastic deformation when said arms are bent into general alignment with said stem during loading of the device into an inserter tube, and having a compressible loop at an end of said stem axially remote from said arms for supporting the device on the upper edges of the cervical os, a portion of said stem adjacent said compressible loop being of reduced thickness.

2. The intrauterine contraceptive device of claim 1 in which a tip of each said arm is enlarged with respect to the remainder of the arm.

3. The intrauterine device of claim 1 wherein tip portions of said arms are rounded in shape.

4. An intrauterine contraceptive device for placement within the uterine cavity having a normally generally T-shaped configuration with a stem having two outwardly extending arms joined to the stem along a smoothly bent curved portion, said curved portion being flexible, said arms normally extending at acute angles with respect to said stem, said smoothly bent curved portion being bent on a sufficient radius of curvature for prevention of plastic deformation when said arms are bent into general alignment with said stem during loading of the device into an inserter tube, and having a compressible loop at an end of said stem axially remote from said arms for supporting the device on the upper edges of the cervical os, wherein said loop and a portion of said stem adjacent said loop are thinner than the rest of said stem for increased flexibility in response to pressure on the device.

5. An intrauterine contraceptive device for placement within the uterine cavity having a normally generally T-shaped configuration with a stem having two outwardly extending arms joined to said stem along a smoothly curved bent portion, said curved portion being flexible, said arms normally extending at acute angles with respect to said stem, and having a compressible loop at an end of said stem axially remote from said arms for supporting the device on the upper edges of the cervical os, a portion of said stem adjacent said loop being of reduced thickness.

* * * * *